United States Patent
de Rougé

(10) Patent No.: US 6,610,304 B1
(45) Date of Patent: Aug. 26, 2003

(54) LIPOSOMES CONTAINING MULTIPLE BRANCH PEPTIDE CONSTRUCTIONS FOR USE AGAINST HUMAN IMMUNODEFICIENCY VIRUS

(76) Inventor: Bonabes-Olivier de Rougé, 116, avenue Félix Faure, F-75015 Paris (FR)

( * ) Notice: Subject to any disclaimer, the term of this patent is extended or adjusted under 35 U.S.C. 154(b) by 37 days.

(21) Appl. No.: 09/607,726

(22) Filed: Jun. 30, 2000

Related U.S. Application Data

(63) Continuation of application No. PCT/EP98/08579, filed on Dec. 28, 1998.

(30) Foreign Application Priority Data

Dec. 31, 1997 (GB) .............................................. 9727424

(51) Int. Cl.⁷ .............................................. A61K 39/21
(52) U.S. Cl. ................................ 424/208.1; 424/204.1; 424/278.1; 424/283.1; 530/327; 530/328; 530/329; 530/330
(58) Field of Search ........................... 424/204.1, 208.1, 424/278.1, 283.1; 530/327–330

(56) References Cited

U.S. PATENT DOCUMENTS 5,709,879 A * 1/1998 Barchfeld et al. .......... 424/450

FOREIGN PATENT DOCUMENTS

| WO | 95/07929 | * 3/1995 |
| WO | 98/29443 | * 7/1998 |
| WO | 99/34777 | * 7/1999 |

* cited by examiner

*Primary Examiner*—Jeffrey Stucker
(74) *Attorney, Agent, or Firm*—Cherskov & Flaynik

(57) ABSTRACT

The incorporation of multiple branch peptide constructions having activity against HIV into liposomes of sufficient size for white blood cell internalization (e.g. greater than 150 nm and preferably approximately 250–400 nm.) has been shown to increase the activity of those MBPCs manifold. The liposomes and pharmaceutical compositions are described herein.

22 Claims, 1 Drawing Sheet

LIPOSOMES CONTAINING MULTIPLE BRANCH PEPTIDE CONSTRUCTIONS FOR USE AGAINST HUMAN IMMUNODEFICIENCY VIRUS

This is a Continuation of PCT/EP98/08579, filed Dec. 28, 1998. This Application claims priority pursuant to 35 U.S.C. 120.

This application claims priority per 35 U.S.C. Section 119(a) and section 365 to Great Britain Patent Application Number GB9727424.5.

DESCRIPTION

The invention relates to liposomes which contain multiple branch peptide constructions (MBPCs) for use in the treatment of Human Immunodeficiency Virus (HIV) infections. The presentation of the MBPCs in liposomes substantially increases their activity.

MBPCs are a recent development in the search for a treatment for HIV infections. Essentially an MBPC comprises a core matrix to which are bonded from 2 to 64, and preferably from 4 to 16 peptides. The core matrix is a dendritic polymer which is branched in nature, preferably with each of the branches thereof being identical. The core matrix is based on a core molecule which has at least two functional groups to which molecular branches having terminal functional groups are covalently bonded. Suitable core molecules include ammonia or ethylenediamine. Suitable molecular branches include acrylic ester monomers which are polymerized onto the core molecule. Such molecules may be created to present varying number of branches, depending on the number of monomers branched from the core molecule. The preferred core molecule is lysine. A central lysine residue is bonded to two lysine residues, each through its carboxyl group, to one of the amino groups of the central lysine residue. This provides a molecule with four amino groups, which may be the core matrix for an MBPC having four peptides. Alternatively, one can provide a molecule with eight branches by bonding four lysine residues through their carboxyl groups to one of the amino groups of the lysine residues which are attached to the central lysine. This molecule can serve as the core matrix for an MBPC having eight peptides or can alternatively receive eight lysine residues to form a core matrix for an MBPC having sixteen peptides.

The C-ends of peptides are covalently bonded to each of the branches of the core matrix to form the MBPC. The peptides may be the same, which is preferred, or may be different from one another. The resulting molecule has a cluster of peptides at the surface and an interior core matrix which is not presented and is therefore not but the L amino acids have better activity. Moreover, peptide analogues, synthetic constructs using the carbon skeleton of peptides but omitting the —CONH— peptide bonds, can be employed in place of peptides. Thus, it should be understood that references to peptides herein may also be taken to include peptide analogues. It is believed that peptide analogues will be more resistant to peptidase and last longer in vivo. If the peptide is too long, the MBPC will become antigenic. It is therefore desirable that each peptide should have not more than ten, and preferably not more than nine, amino acid residues.

MBPCs for use in the treatment of HIV infections were first described by J-M. Sabatier et al in WO 95/07929. The MBPCs described therein have peptides which contain the sequence GPGR (SEQ. ID. NO. 1)(from the V3 loop of the surface envelope glycoprotein gp120 of HIV) preceded by from 0 to 4 amino acid residues and succeeded by from 2 to 4 amino acid residues. The amino acid sequences IGPGR (SEQ. ID. NO. 2) and IXXGPGR (SEQ. ID. NO. 3)(where X is an amino acid residue) are excluded. The most preferred of these MBPCs has a lysine residue core with eight peptides GPGRAF (SEQ. ID. NO. 4) bonded thereto. It may be represented as $(GPGRAF)_8\text{-}(K)_4\text{-}(K)_2\text{-}K\text{-}\beta A\text{-}OH$, the OH terminal indicating the carboxyl group of the β-alanine. That carboxyl group may alternatively be modified to form a carboxamide terminal. This compound is referred to herein as SPC3. These MBPCs and SPC3 in particular have been found to interfere with the virus envelope—cell membrane fusion step and also the infected cell membrane—uninfected cell membrane fusion step, either step being thought to be indispensable for cell infection, virus multiplication and the spread of virus in the host organism, by blockading the CD4 receptor present in cells such as lymphocytes and macrophages, possibly by attaching to a membrane co-receptor which is distinct from the CD4 binding receptor, without causing the cell to lose its ability to be activated by other antigens or mitogens.

More recently, in WO 98/29443, J-M Sabatier et al have described further MBPCs which may be effective in the treatment of HIV infection. These use peptides derived from the HIV envelope transmembrane glycoprotein gp41. The peptides contain the sequence RQGY (SEQ. ID. NO. 5) preceded by from 0 to 4 amino acid residues and succeeded by from 2 to 4 amino acid residues. The most preferred of these MBPCs has a lysine residue core with eight peptides RQGYSPL (SEQ. ID. NO. 6) bonded thereto. It may be represented as $(RQGYSPL)_8\text{-}(K)_4\text{-}(K)_2\text{-}K\text{-}\beta A\text{-}OH$, the OH terminal indicating the carboxyl group of the β-alanine. That carboxyl group may alternatively be modified to form a carboxamide terminal. This compound is referred to herein as SPC RL. These MBPCs and SPC RL in particular are also believed to interfere with a critical step of the virus—cell fusion process.

SUMMARY OF THE INVENTION

The invention provides liposomes having a sufficient size for while blood cell internalisation, the liposomes containing an MBPC which is useful for the treatment of HIV. Naturally, the preferred MBPCs at present are those disclosed in WO 95/07929 and WO 98/29443, having a lysine core and 8 to 16 peptides incorporating GPGR (SEQ. ID. NO. 1)(but not IGPGR (SEQ. ID. NO. 2) or IXXGPGR) (SEQ. ID. NO. 3) or ROGY (SEQ. ID. NO. 5). Most preferred are those in which the peptides are GPGRAF (SEQ. ID. NO. 4) and RQGYSPL (SEQ. ID. NO. 6), especially SPC3 and SPC RL.

The invention also provides a pharmaceutical composition containing liposomes according to the invention in admixture with a pharmaceutically acceptable carrier. The preferred pharmaceutically acceptable carrier is 0.9% sterile saline, although any suitable carrier for liposome suspension storage and for injection into humans may be used. The pharmaceutical composition according to the invention preferably contains the MBPC in an amount of at least 10 mg/mil so as to keep injection volumes low.

The invention further provides a method for the treatment of a patient having HIV infection, the method comprising administering a pharmaceutical composition according to the invention to the patient by intravenous injection. A likely dosage is from 20 to 100 mg, preferably from 20 to 60 mg of the active ingredient, given at intervals varying from once a day to once a week, according to the viral load. It is anticipated that treatment may not need to be continuous (though it can be), but may be given in courses of from three weeks to one month, then interrupted until the viral load comes up again. Patients would continue to take their current treatment (tritherapies and the like) during and after treatment according to the invention. Because the mode of action of MBPCs makes them independent from viral strain, resistance to the MBPCs should not appear. It should therefore be possible to repeat the treatment, which is currently not possible with RT or protease inhibitors.

BRIEF DESCRIPTION OF THE DRAWING

Other objects, features, and advantages of the present invention will become apparent from the following description and the accompanying drawing, wherein.

DETAILED DESCRIPTION OF THE INVENTION

Figure 1:
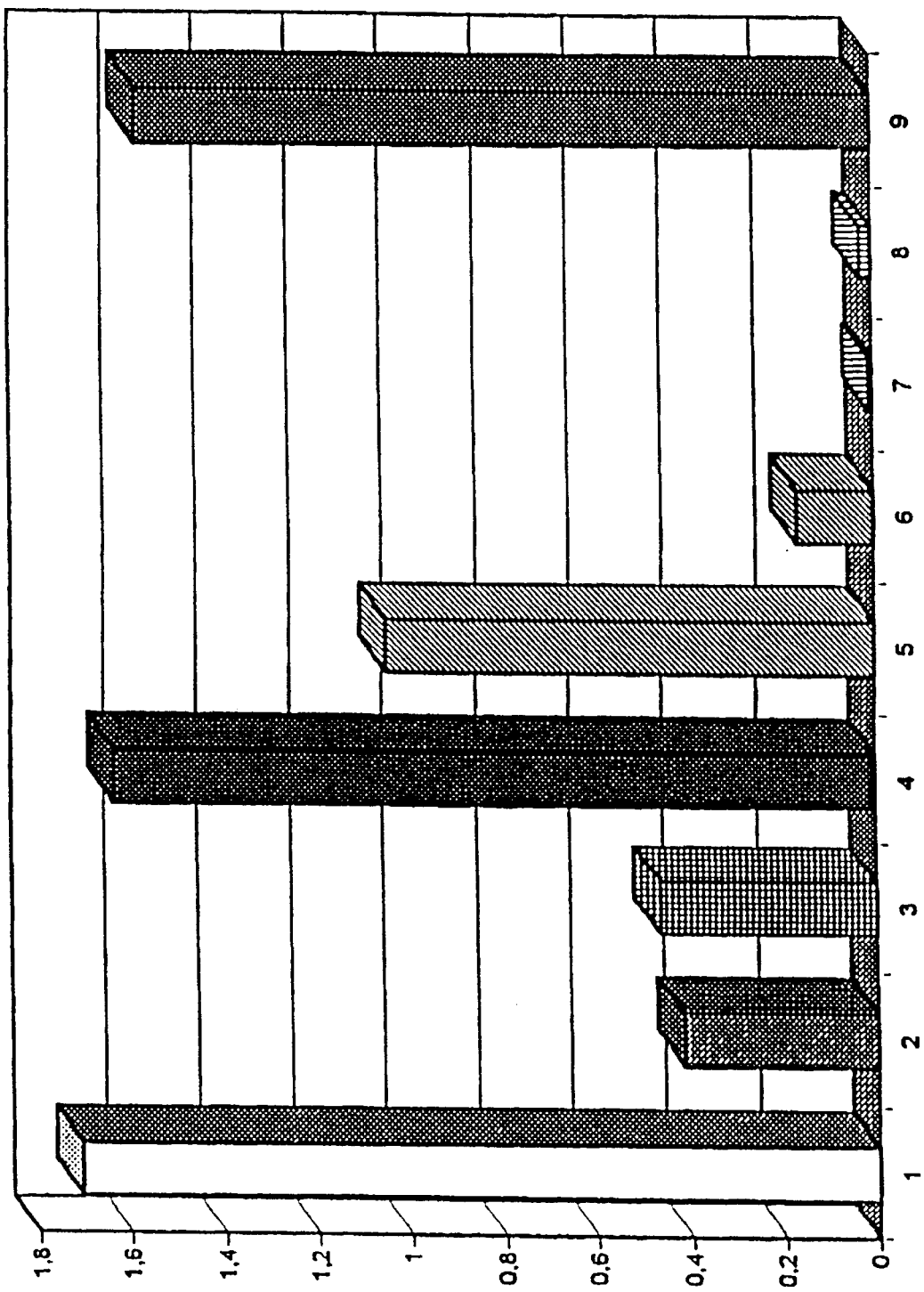
FIG. 1 is a graphical depiction of HIV infection in cells exposed to the invented composition, in accordance with features of the present invention.

The incorporation of anti-HIV MBPCs such as SPC3 and SPC RL into liposomes is intended to make them more available to the lymphatic system and to the lymphocytes and macrophages which are the target cells for HIV and therefore for anti-HIV substances. Early clinical data has shown that SPC3 has a certain activity in HIV-infected patients, but usually insufficient activity at the doses used (20 mg/day i.v.). Although it was postulated that these MBPCs act on a membrane receptor, it was not known whether they actually acted from the inside or the outside of the membrane. If from the inside, the very high hydrophilicity of the free peptides would make them poor candidates for internalisation, and incorporation into liposomes might enable the MBPCs to enter the cells more readily. Very small liposomes, e.g. those under 100 to 150 nm in diameter are not readily captured by white blood cells, so larger liposomes having a size of greater than 150 nm average diameter are preferred. Liposomes having approximately 250 to 400 nm average diameter are most preferred.

Liposomes according to the invention may be prepared by any conventional method, but the method of Bangham et al., J. Mol. Biol., 13, 238–252, (1964) is preferred. The liposomes may be extruded through calibrated filters in order to obtain desired sizes. The liposomes may be dialysed to remove MBPCs which have not been incorporated but which have remained electrostatically bound to the external surface of the liposomes. Preferably the liposomes encapsulate at much of the MBPC as possible (above 8% after dialysis) so as enable the aforedescribed MBPC concentration in the injection formulation to be achieved and thus to keep injection volumes low. The liposomes may be formulated from egg phosphliatidyiclholine and phosphatidylglycerol in a molar ratio of from 4:1 to 20:1, but preferably 9:1.

The antiviral activity of liposomes containing SPC3 has been investigated in comparison with that of empty liposomes, SPC3 and SPC RL. The liposomes containing SPC3 were tested both after dialysis and without dialysis, to determine the effect of SPC3 electrostatically bound to the liposome outside surface. In all tests, the amounts of SPC3 in the liposomic formulations was the same as the amount used in free form.

Fusion Assay: Inhibition of Syncytium Formation

C8166 cells were incubated at 37° C. with HIV-1 Hx10 clone (B. Hahn, University of Alabama, USA) in the presence of test substances (SPC3, SPC RL, empty liposomes of 110 nm and 250 nm average size, and dialysed and non-dialysed liposomes of those sizes containing SPC3) and in the absence of any test substance (control). The samples were inspected by phase contrast microscopy and syncytia were scored after 48 and 72 hours of incubation in 96-well flat-bottomed cultured plates. Experiments were performed three times in duplicate and identical results were obtained. The results are shown in Table 1 below. The presence of syncytia is indicated by + signs. allocated as follows:

+++=control
++=50% decrease
+=90% decrease
+/−=>95 % decrease

TABLE 1

| | Syncitia Formation | | | |
|---|---|---|---|---|
| | Day 2 post-infection Concentration | | Day 3 post-infection Concentration | |
| Test Substance | $10^{-5}$ M | $10^{-6}$ M | $10^{-5}$ M | $10^{-6}$ M |
| None (Control) | +++ | +++ | +++ | +++ |
| SPC3 | − | +/− | − | +/− |
| SPC RL | − | +/− | − | +/− |
| Liposome, 100 mn, empty | +++ | +++ | +++ | +++ |
| Liposome, 100 nm, SPC3, dialysed | − | +/− | − | +++ |
| Liposome, 100 nm, SPC3, non-dialysed | − | +/− | − | + |
| Liposome, 250 nm, empty | +++ | +++ | +++ | +++ |
| Liposome, 250 nm, SPC3, dialysed | − | − | − | − |
| Liposome, 250 nm, SPC3, non-dialysed | − | − | − | − |

Infection Assay: Inhibition of Cell Infection

C8166 cells were washed once in RPMI medium and then infected with HIV-1 Hx10clone by incubation at 37° C. for 2 hours in the presence of test substances (SPC3, SPC RL, empty liposomes of 110 nm and 250 nm average size, and dialysed and non-dialysed liposomes of those sizes containing SPC3) and in the absence of any test substance (control). After incubation, the virus was removed and the cells were incubated with fresh medium at 37° C. in the presence of the test substances or in the absence of any test substance (control). Infections and cell cultures were in 96-well culture plates. The production of HIV was monitored by measuring the concentration of cell-free p24 in the supernatant by ELISA, as described by Gluschankof et al., 1997, using the AMPAK amplification kit (DAKO. Trappes, France). The results are shown in Table 2 below, and the day 4 results are also shown graphically in the accompanying drawing.

TABLE 2

| | p24 production | | |
|---|---|---|---|
| No. of Bar in Figure | Administered Substance | Day 3 post-infection | Day 4 post-infection |
| 1 | None (Control) | 1.633 | 1.705 |
| 2 | SPC3 | 0.400 | 0.415 |
| 3 | SPC RL | 0.441 | 0.463 |
| 4 | Liposome, 100 nm, empty | 1.614 | 1.633 |
| 5 | Liposome, 100 nm, SPC3, dialysed | 0.934 | 1.047 |
| 6 | Liposome, 100 nm, SPC3, non-dialysed | 0.124 | 0.166 |
| 9 | Liposome, 250 nm, empty | 1.539 | 1.581 |

TABLE 2-continued p24 production

| No. of Bar in Figure | Administered Substance | Day 3 post-infection | Day 4 post-infection |
|---|---|---|---|
| 8 | Liposome, 250 nm, SPC3, dialysed | 0.049 (= 0.32 ng/ml) | 0.024 |
| 7 | Liposome, 250 nm, SPC3, non-dialysed | 0.046 (= 0.28 ng/ml) | 0.008 |

The 100 nm liposomes containing SPC3 and dialysed had an activity weaker than SPC itself, although there was a three fold increase in activity when these liposomes were used without dialysis. As very small liposomes, under 100–150 nm in diameter, are not readily captured by white blood cells, and therefore not internalised, these results are not surprising or significant. However, the 250 nm liposomes containing SPC3 have produced results which are truly outstanding. Considering the non-dialysed formulations, there is an 8.7 fold improvement over free SPC3 by day 3 in the infection assay and a 52 fold improvement over free SPC3 by day 4. There is a small difference in activity between the dialysed and non-dialysed liposomes, not statistically significant but slightly in favour of non-dialysed formulations. These 250 nm liposomes very potent inhibitors of HIV infection in both the fusion (syncytia formation) and infection assays. In both cases, the antiviral properties appear to be clearly superior to those observed with free SPC3.

Toxicity

To determine toxicity, the 250 nm dialysed liposomes containing SPC3 were injected intravenously into 8 mice at a dose of 50 mg/kg of SPC3. It will be noted that this is an extremely high dose, about 50 times higher than the dosages suggested above. No symptoms were detected either immediately or after 12 or 24 hours. Using free SPC3, symptoms of toxicity were observed at this dose.

The incorporation of a peptide into a liposome was not expected to increase its activity in vitro (i.e. independently of any improvement in the distribution, metabolism or organ targeting properties) by such an order of magnitude. It is not known at this stage whether the improvement is due to an improvement of the activity in the already postulated mode of action (blocking of the fusion reception for HIV), or through other intra-cellular mechanisms. Either way, SPC3 delivered in liposomes could be much more useful than free SPC3 in the treatment of HIV infections because the daily dose can be greatly reduced avoiding adverse side effects, because the toxicity appears less than that of free SPC3 and because the dose administration schedule can be modified, for instance becoming weekly instead of daily. This makes SPC3 a better candidate for becoming part of an anti-HIV therapeutic strategy, despite the fact that it has to be administered intravenously.

The embodiment of the invention in which an exclusive property or privilege is claimed is defined as follows:

1. Liposomes having a sufficient size for white blood cell internalization, wherein the liposomes contain multiple branch peptide constructions.

2. The liposomes as recited in claim 1, wherein the liposomes have an average size of greater than 150 nm.

3. The liposomes as recited in claim 1, wherein the liposomes have an average size of between 250 nm and 400 nm.

4. The liposomes as recited in claim 1, wherein above 8% of the weight of the liposomes is the multiple branch peptide constructions.

5. The liposomes as recited in claim 1, wherein the multiple branch peptide constructions have a lysine core.

6. The liposomes as recited in claim 1, wherein the multiple branch peptide constructions have 8 peptides.

7. The liposomes as recited in claim 1, wherein the multiple branch peptide constructions have 16 peptides.

8. The liposomes as recited in claim 1, wherein the peptides have the sequence GPGR (SEQ. ID. NO. 1) preceded by from between 0 to 4 amino acid residues and succeeded by between 2 to 4 amino acid residues, but do not contain either of the sequences IGPGR (SEQ. ID. NO. 2) or IXXGPGR (SEQ. ID. NO. 3), where X is an amino acid residue.

9. The liposomes as recited in claim 1, wherein the peptides are GPGRAF (SEQ. ID. NO. 4).

10. The liposomes as recited in claim 6, wherein the multiple branch peptide constructions are SPC3.

11. The liposomes as recited in claim 7, wherein the multiple branch peptide constructions are SPC3.

12. The liposomes as recited in claim 1, wherein the peptides have the sequence RQGY (SEQ. ID. NO. 5) preceded by between 0 to 4 amino acid residues and succeeded by between 2 to 4 amino acid residues.

13. The liposomes as recited in claim 1, wherein the peptides are RQGYSPL (SEQ. ID. NO. 6).

14. The liposomes as recited in claim 1, wherein the multiple branch peptide constructions are SPC RL.

15. The liposomes as recited in claim 1, in admixture with a carrier to create a pharmaceutically acceptable composition.

16. A method for the treatment of a patient having HIV infection, the method comprising administering the pharmaceutical composition recited in claim 14 to the patient by intravenous injection.

17. A method for treating patients infected with HIV, the method comprising intravenously injecting the patient with a pharmaceutical composition comprising liposomes having a sufficient size for white blood cell internalization and containing multiple branch peptide constructions.

18. The method as recited in claim 17, wherein the average size is greater than 150 nm.

19. The method as recited in claim 17, wherein liposome size ranges from between approximately 250 nm and 400 nm.

20. The method as recited in claim 17, wherein above 8% of the weight of the liposomes is the multiple branch peptide constructions.

21. The method as recited in claim 17, wherein the multiple branch peptide constructions are SPC RL.

22. The method as recited in claim 17, wherein the multiple branch peptide constructions are SPC3.

* * * * *

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
      (A) LENGTH: 4 amino acids
      (B) TYPE: amino acid
      (C) STRANDEDNESS: single
      (D) TOPOLOGY: linear (xi) SEQUENCE DESCRIPTION: SEQ ID NO: 1:

Gly Pro Gly Arg (2) INFORMATION FOR SEQ ID NO: 2:

(i) SEQUENCE CHARACTERISTICS:
      (A) LENGTH: 5 amino acids
      (B) TYPE: amino acid
      (C) STRANDEDNESS: single
      (D) TOPOLOGY: linear (xi) SEQUENCE DESCRIPTION: SEQ ID NO: 2:

Ile Gly Pro Gly Arg
1           5

(2) INFORMATION FOR SEQ ID NO: 3:

(i) SEQUENCE CHARACTERISTICS:
      (A) LENGTH: 7 amino acids
      (B) TYPE: amino acid
      (C) STRANDEDNESS: single

```
            (D) TOPOLOGY: linear (xi) SEQUENCE DESCRIPTION: SEQ ID NO: 3:

Ile Xaa Xaa Gly Pro Gly Arg
1               5

(2) INFORMATION FOR SEQ ID NO: 4:

(i) SEQUENCE CHARACTERISTICS:
            (A) LENGTH: 6 amino acids
            (B) TYPE: amino acid
            (C) STRANDEDNESS: single
            (D) TOPOLOGY: linear (xi) SEQUENCE DESCRIPTION: SEQ ID NO: 4:

Gly Pro Gly Arg Ala Phe
1               5

(2) INFORMATION FOR SEQ ID NO: 5:

(i) SEQUENCE CHARACTERISTICS:
            (A) LENGTH: 4 amino acids
            (B) TYPE: amino acid
            (C) STRANDEDNESS: single
            (D) TOPOLOGY: linear (xi) SEQUENCE DESCRIPTION: SEQ ID NO: 5:

Arg Gln Gly Tyr (2) INFORMATION FOR SEQ ID NO: 6:

(i) SEQUENCE CHARACTERISTICS:
            (A) LENGTH: 7 amino acids
            (B) TYPE: amino acid
            (C) STRANDEDNESS: single
            (D) TOPOLOGY: linear (xi) SEQUENCE DESCRIPTION: SEQ ID NO: 6:

Arg Gln Gly Tyr Ser Pro Leu
1               5
```